United States Patent
Dittmann et al.

(10) Patent No.: US 11,045,331 B2
(45) Date of Patent: Jun. 29, 2021

(54) INTERVERTEBRAL IMPLANT INSERTERS AND RELATED METHODS

(71) Applicant: DePuy Synthes Products, Inc., Raynham, MA (US)

(72) Inventors: Dirk Dittmann, Basel (CH); William Miller, Middleboro, MA (US); Jeff Walker, Barrington, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/103,136

(22) Filed: Aug. 14, 2018

(65) Prior Publication Data
US 2019/0046334 A1    Feb. 14, 2019

Related U.S. Application Data

(60) Provisional application No. 62/544,997, filed on Aug. 14, 2017.

(51) Int. Cl.
*A61F 2/46* (2006.01)
*A61F 2/44* (2006.01)

(52) U.S. Cl.
CPC ............ *A61F 2/4611* (2013.01); *A61F 2/442* (2013.01); *A61F 2/4455* (2013.01); *A61F 2002/4627* (2013.01); *A61F 2002/4629* (2013.01)

(58) Field of Classification Search
CPC ....... A61F 2/4611; A61F 2/442; A61F 2/4455
USPC .................................. 606/99, 86 A
See application file for complete search history.

(56) References Cited

U.S. PATENT DOCUMENTS

| 3,426,364 A | 2/1969 | Lumb |
| 3,867,728 A | 2/1975 | Stubstad et al. |
| 4,105,034 A | 8/1978 | Shalaby et al. |
| 4,130,639 A | 12/1978 | Shalaby et al. |

(Continued)

FOREIGN PATENT DOCUMENTS

| CA | 2446934 A1 | 11/2002 |
| CA | 2534357 A1 | 2/2005 |

(Continued)

OTHER PUBLICATIONS

AcroMed Carbon Fiber Interbody Fusion Devices; Jan. 1998, 8 pages.

(Continued)

*Primary Examiner* — Si Ming Ku
(74) *Attorney, Agent, or Firm* — Nutter McClennen & Fish LLP

(57) ABSTRACT

Implant inserters and related methods are disclosed herein, e.g., for delivering a fusion cage or other implant to a spinal disc space and for rotating or articulating the implant within the disc space. An exemplary instrument can include an inner member having opposed jaws for grasping the implant and holding the implant during insertion. The inner member can be slidably received within an outer member such that relative axial translation of the inner and outer members is effective to open or close the jaws. The jaws and/or the distal end of the outer member can have a low-profile geometry, which can advantageously facilitate certain surgical procedures. For example, the low-profile geometry can allow for a more medial approach to an intervertebral disc space in which the implant is to be inserted.

15 Claims, 7 Drawing Sheets

(56) References Cited

U.S. PATENT DOCUMENTS

| | | |
|---|---|---|
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,298,993 A | 11/1981 | Kovaleva et al. |
| 4,349,921 A | 9/1982 | Kuntz |
| 4,394,370 A | 7/1983 | Jefferies |
| 4,450,591 A | 5/1984 | Rappaport |
| 4,454,374 A | 6/1984 | Pollack |
| 4,538,612 A | 9/1985 | Patrick, Jr. |
| 4,545,374 A | 10/1985 | Jacobson |
| 4,599,086 A | 7/1986 | Doty |
| 4,627,853 A | 12/1986 | Campbell et al. |
| 4,714,469 A | 12/1987 | Kenna |
| 4,743,256 A | 5/1988 | Brantigan |
| 4,781,721 A | 11/1988 | Grundei |
| 4,829,152 A | 5/1989 | Rostoker et al. |
| 4,834,757 A | 5/1989 | Brantigan |
| 4,863,476 A | 9/1989 | Shepperd |
| 4,872,452 A | 10/1989 | Alexson |
| 4,877,020 A | 10/1989 | Vich et al. |
| 4,878,915 A | 11/1989 | Brantigan |
| 4,904,261 A | 2/1990 | Dove et al. |
| 4,911,718 A | 3/1990 | Lee et al. |
| 4,917,704 A | 4/1990 | Frey et al. |
| 4,927,425 A | 5/1990 | Lozier |
| 4,941,481 A | 7/1990 | Wagenknecht |
| 4,955,908 A | 9/1990 | Frey et al. |
| 4,995,200 A | 2/1991 | Eberhart |
| 4,997,432 A | 3/1991 | Keller |
| 5,006,120 A | 4/1991 | Carter |
| 5,006,121 A | 4/1991 | Hafeli |
| 5,015,247 A | 5/1991 | Michelson |
| 5,019,082 A | 5/1991 | Frey et al. |
| 5,047,058 A | 9/1991 | Roberts et al. |
| 5,116,374 A | 5/1992 | Stone |
| 5,123,926 A | 6/1992 | Pisharodi |
| 5,133,719 A | 7/1992 | Winston |
| 5,163,939 A | 11/1992 | Winston |
| 5,169,402 A | 12/1992 | Elloy |
| 5,171,240 A | 12/1992 | Hanwong |
| 5,171,278 A | 12/1992 | Pisharodi |
| 5,171,281 A | 12/1992 | Parsons et al. |
| 5,190,549 A | 3/1993 | Miller et al. |
| 5,192,327 A | 3/1993 | Brantigan |
| 5,201,736 A | 4/1993 | Strauss |
| 5,217,475 A | 6/1993 | Kuber |
| 5,250,061 A | 10/1993 | Michelson |
| 5,258,031 A | 11/1993 | Salib et al. |
| 5,282,861 A | 2/1994 | Kaplan |
| 5,298,254 A | 3/1994 | Prewett et al. |
| 5,306,307 A | 4/1994 | Senter et al. |
| 5,306,308 A | 4/1994 | Gross et al. |
| 5,306,309 A | 4/1994 | Wagner et al. |
| 5,320,644 A | 6/1994 | Baumgartner |
| 5,342,365 A | 8/1994 | Waldman |
| 5,387,215 A | 2/1995 | Fisher |
| 5,390,683 A | 2/1995 | Pisharodi |
| 5,397,364 A | 3/1995 | Kozak et al. |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,454,815 A | 10/1995 | Geisser et al. |
| 5,454,827 A | 10/1995 | Aust et al. |
| 5,464,929 A | 11/1995 | Bezwada et al. |
| 5,476,466 A | 12/1995 | Barrette et al. |
| 5,484,437 A | 1/1996 | Michelson |
| 5,522,899 A | 6/1996 | Michelson |
| 5,540,693 A | 7/1996 | Fisher |
| 5,545,229 A | 8/1996 | Parsons et al. |
| 5,550,172 A | 8/1996 | Regula et al. |
| 5,554,191 A | 9/1996 | Lahille |
| 5,556,431 A | 9/1996 | Buttner-Janz |
| 5,595,751 A | 1/1997 | Bezwada et al. |
| 5,597,579 A | 1/1997 | Bezwada et al. |
| 5,601,561 A | 2/1997 | Terry et al. |
| 5,607,687 A | 3/1997 | Bezwada et al. |
| 5,609,635 A | 3/1997 | Michelson |
| 5,618,552 A | 4/1997 | Bezwada et al. |
| 5,620,448 A | 4/1997 | Puddu |
| 5,620,698 A | 4/1997 | Bezwada et al. |
| 5,645,596 A | 7/1997 | Kim et al. |
| 5,645,850 A | 7/1997 | Bezwada et al. |
| 5,648,088 A | 7/1997 | Bezwada et al. |
| 5,658,335 A | 8/1997 | Allen |
| 5,658,336 A | 8/1997 | Pisharodi |
| 5,665,122 A | 9/1997 | Kambin |
| 5,669,909 A | 9/1997 | Zdeblick et al. |
| 5,674,296 A | 10/1997 | Bryan et al. |
| 5,683,463 A | 11/1997 | Godefroy et al. |
| 5,693,100 A | 12/1997 | Pisharodi |
| 5,698,213 A | 12/1997 | Jamiolkowski et al. |
| 5,700,583 A | 12/1997 | Jamiolkowski et al. |
| 5,702,449 A | 12/1997 | McKay |
| 5,702,463 A | 12/1997 | Pothier et al. |
| 5,707,371 A | 1/1998 | Metz-Stavenhagen et al. |
| 5,725,531 A | 3/1998 | Shapiro |
| 5,728,159 A | 3/1998 | Stroever et al. |
| 5,755,798 A | 5/1998 | Papavero et al. |
| 5,766,251 A | 6/1998 | Koshino |
| 5,766,252 A | 6/1998 | Henry et al. |
| 5,772,661 A | 6/1998 | Michelson |
| 5,782,830 A | 7/1998 | Farris |
| 5,782,919 A | 7/1998 | Zdeblick et al. |
| 5,836,948 A | 11/1998 | Zucherman et al. |
| 5,857,995 A | 1/1999 | Thomas et al. |
| 5,859,150 A | 1/1999 | Jamiolkowski et al. |
| 5,860,973 A | 1/1999 | Michelson |
| 5,865,845 A | 2/1999 | Thalgott |
| 5,865,848 A | 2/1999 | Baker |
| 5,888,222 A | 3/1999 | Coates et al. |
| 5,888,223 A | 3/1999 | Bray, Jr. |
| 5,893,890 A | 4/1999 | Pisharodi |
| 5,906,616 A | 5/1999 | Pavlov et al. |
| 5,916,228 A | 6/1999 | Ripich et al. |
| 5,925,056 A | 7/1999 | Thomas et al. |
| 5,964,807 A | 10/1999 | Gan et al. |
| 5,968,098 A | 10/1999 | Winslow |
| 5,976,187 A | 11/1999 | Richelsoph |
| 5,980,522 A | 11/1999 | Koros et al. |
| 5,989,289 A | 11/1999 | Coates et al. |
| 6,001,099 A | 12/1999 | Huebner |
| 6,008,433 A | 12/1999 | Stone |
| 6,039,761 A | 3/2000 | Li et al. |
| 6,039,762 A | 3/2000 | McKay |
| 6,045,579 A | 4/2000 | Hochshuler et al. |
| 6,053,922 A | 4/2000 | Krause et al. |
| 6,056,763 A | 5/2000 | Parsons |
| 6,066,174 A | 5/2000 | Farris |
| 6,066,175 A | 5/2000 | Henderson et al. |
| 6,080,158 A | 6/2000 | Lin |
| 6,086,593 A | 7/2000 | Bonutti |
| 6,099,531 A | 8/2000 | Bonutti |
| 6,106,557 A | 8/2000 | Robioneck et al. |
| 6,120,508 A | 9/2000 | Grunig et al. |
| 6,126,689 A | 10/2000 | Brett |
| 6,139,558 A | 10/2000 | Wagner |
| 6,143,032 A | 11/2000 | Schafer et al. |
| 6,146,421 A | 11/2000 | Gordon et al. |
| 6,159,215 A | 12/2000 | Urbahns et al. |
| 6,174,311 B1 | 1/2001 | Branch et al. |
| 6,176,882 B1 | 1/2001 | Biedermann et al. |
| 6,206,922 B1 | 3/2001 | Zdeblick et al. |
| 6,231,610 B1 | 5/2001 | Geisler |
| 6,235,059 B1 | 5/2001 | Benezech et al. |
| 6,241,733 B1 | 6/2001 | Nicholson et al. |
| 6,245,108 B1 | 6/2001 | Biscup |
| 6,251,140 B1 | 6/2001 | Marino et al. |
| 6,258,093 B1 | 7/2001 | Edwards et al. |
| 6,296,644 B1 | 10/2001 | Saurat et al. |
| 6,309,421 B1 | 10/2001 | Pisharodi |
| D450,676 S | 11/2001 | Huttner |

(56) References Cited

U.S. PATENT DOCUMENTS

| | | | |
|---|---|---|---|
| 6,319,257 B1 * | 11/2001 | Carignan | A61F 2/4601 606/205 |
| 6,332,894 B1 | 12/2001 | Stalcup et al. | |
| 6,342,074 B1 | 1/2002 | Simpson | |
| 6,364,880 B1 | 4/2002 | Michelson | |
| 6,371,988 B1 | 4/2002 | Pafford et al. | |
| 6,387,130 B1 | 5/2002 | Stone et al. | |
| 6,398,793 B1 | 6/2002 | McGuire | |
| 6,409,766 B1 | 6/2002 | Brett | |
| 6,413,278 B1 | 7/2002 | Marchosky | |
| 6,423,095 B1 | 7/2002 | Van Hoeck et al. | |
| 6,425,920 B1 | 7/2002 | Hamada | |
| 6,428,544 B1 | 8/2002 | Ralph et al. | |
| 6,432,106 B1 | 8/2002 | Fraser | |
| 6,436,101 B1 | 8/2002 | Hamada | |
| 6,443,987 B1 | 9/2002 | Bryan | |
| 6,447,518 B1 | 9/2002 | Krause et al. | |
| 6,447,544 B1 | 9/2002 | Michelson | |
| 6,482,233 B1 | 11/2002 | Aebi et al. | |
| 6,511,509 B1 | 1/2003 | Ford et al. | |
| 6,579,318 B2 | 6/2003 | Varga et al. | |
| 6,582,432 B1 | 6/2003 | Michelson | |
| 6,595,998 B2 | 7/2003 | Johnson et al. | |
| 6,599,294 B2 | 7/2003 | Fuss et al. | |
| 6,605,089 B1 | 8/2003 | Michelson | |
| 6,610,066 B2 | 8/2003 | Dinger et al. | |
| 6,610,089 B1 | 8/2003 | Liu et al. | |
| 6,635,060 B2 | 10/2003 | Hanson et al. | |
| RE38,335 E | 11/2003 | Aust et al. | |
| 6,641,582 B1 | 11/2003 | Hanson et al. | |
| 6,648,915 B2 | 11/2003 | Sazy | |
| 6,660,004 B2 | 12/2003 | Barker et al. | |
| 6,676,703 B2 | 1/2004 | Biscup | |
| 6,699,288 B2 | 3/2004 | Moret et al. | |
| 6,719,794 B2 | 4/2004 | Gerber et al. | |
| 6,733,535 B2 | 5/2004 | Michelson | |
| 6,746,484 B1 | 6/2004 | Liu et al. | |
| 6,755,837 B2 | 6/2004 | Ebner | |
| 6,764,491 B2 | 7/2004 | Frey | |
| 6,767,366 B2 | 7/2004 | Lee et al. | |
| 6,830,570 B1 | 12/2004 | Frey et al. | |
| 6,835,206 B2 | 12/2004 | Jackson | |
| 6,835,208 B2 | 12/2004 | Marchosky | |
| 6,840,941 B2 | 1/2005 | Rogers et al. | |
| 6,852,127 B2 | 2/2005 | Varga et al. | |
| 6,878,167 B2 | 4/2005 | Ferree | |
| 6,949,108 B2 | 9/2005 | Holmes | |
| 6,966,912 B2 | 11/2005 | Michelson | |
| 6,974,480 B2 | 12/2005 | Messerli et al. | |
| 7,018,415 B1 | 3/2006 | McKay | |
| 7,048,762 B1 | 5/2006 | Sander et al. | |
| 7,048,765 B1 | 5/2006 | Grooms et al. | |
| 7,060,073 B2 | 6/2006 | Frey et al. | |
| 7,060,096 B1 | 6/2006 | Schopf et al. | |
| 7,066,961 B2 | 6/2006 | Michelson | |
| 7,070,598 B2 | 7/2006 | Lim et al. | |
| 7,087,055 B2 | 8/2006 | Lim et al. | |
| 7,105,024 B2 | 9/2006 | Richelsoph | |
| 7,112,224 B2 | 9/2006 | Liu et al. | |
| 7,115,128 B2 | 10/2006 | Michelson | |
| 7,115,132 B2 | 10/2006 | Errico et al. | |
| 7,125,424 B2 | 10/2006 | Banick et al. | |
| 7,169,182 B2 | 1/2007 | Errico et al. | |
| 7,169,183 B2 | 1/2007 | Liu et al. | |
| 7,192,447 B2 | 3/2007 | Rhoda | |
| 7,223,292 B2 | 5/2007 | Messerli et al. | |
| 7,226,482 B2 | 6/2007 | Messerli et al. | |
| 7,226,483 B2 | 6/2007 | Gerber et al. | |
| 7,229,477 B2 | 6/2007 | Biscup | |
| 7,235,081 B2 | 6/2007 | Errico et al. | |
| 7,235,082 B2 | 6/2007 | Bartish et al. | |
| 7,291,173 B2 | 11/2007 | Richelsoph et al. | |
| 7,311,734 B2 | 12/2007 | Van Hoeck et al. | |
| 7,320,688 B2 | 1/2008 | Foley et al. | |
| 7,326,248 B2 | 2/2008 | Michelson | |
| 7,331,996 B2 | 2/2008 | Sato et al. | |
| 7,351,262 B2 | 4/2008 | Bindseil et al. | |
| 7,361,193 B2 | 4/2008 | Frey et al. | |
| 7,404,795 B2 | 7/2008 | Ralph et al. | |
| 7,465,305 B2 | 12/2008 | Liu et al. | |
| 7,470,273 B2 | 12/2008 | Dougherty-Shah | |
| 7,473,268 B2 | 1/2009 | Zucherman et al. | |
| 7,481,812 B2 | 1/2009 | Frey et al. | |
| 7,491,237 B2 | 2/2009 | Randall et al. | |
| 7,500,991 B2 | 3/2009 | Bartish, Jr. et al. | |
| 7,503,920 B2 | 3/2009 | Siegal | |
| 7,572,279 B2 | 8/2009 | Jackson | |
| 7,575,580 B2 | 8/2009 | Lim et al. | |
| 7,578,820 B2 | 8/2009 | Moore et al. | |
| 7,601,173 B2 | 10/2009 | Messerli et al. | |
| 7,608,080 B2 | 10/2009 | Shipp et al. | |
| 7,618,458 B2 | 11/2009 | Biedermann et al. | |
| 7,625,377 B2 | 12/2009 | Veldhuizen et al. | |
| 7,625,394 B2 | 12/2009 | Molz, IV et al. | |
| 7,655,010 B2 | 2/2010 | Serhan et al. | |
| 7,655,045 B2 | 2/2010 | Richelsoph | |
| 7,666,186 B2 | 2/2010 | Harp | |
| 7,666,226 B2 | 2/2010 | Schaller | |
| 7,670,374 B2 | 3/2010 | Schaller | |
| 7,674,265 B2 | 3/2010 | Smith et al. | |
| 7,682,400 B2 | 3/2010 | Zwirkoski | |
| 7,703,727 B2 | 4/2010 | Selness | |
| 7,704,280 B2 | 4/2010 | Lechmann et al. | |
| 7,731,751 B2 | 6/2010 | Butler et al. | |
| 7,763,028 B2 | 7/2010 | Lim et al. | |
| 7,771,473 B2 | 8/2010 | Thramann | |
| 7,785,368 B2 | 8/2010 | Schaller | |
| 7,799,081 B2 | 9/2010 | McKinley | |
| 7,803,161 B2 | 9/2010 | Foley et al. | |
| 7,806,932 B2 | 10/2010 | Webb et al. | |
| 7,811,292 B2 | 10/2010 | Lo et al. | |
| 7,828,849 B2 | 11/2010 | Lim | |
| 7,832,409 B2 | 11/2010 | Richelsoph et al. | |
| 7,837,734 B2 | 11/2010 | Zucherman et al. | |
| 7,850,733 B2 | 12/2010 | Baynham et al. | |
| 7,875,080 B2 | 1/2011 | Puno et al. | |
| 7,901,458 B2 | 3/2011 | DeRidder et al. | |
| 7,918,874 B2 | 4/2011 | Siegal | |
| 7,922,719 B2 | 4/2011 | Ralph et al. | |
| 7,935,124 B2 | 5/2011 | Frey et al. | |
| 7,935,148 B2 | 5/2011 | Edie et al. | |
| 7,938,857 B2 | 5/2011 | Garcia-Bengochea et al. | |
| 7,942,903 B2 | 5/2011 | Moskowitz et al. | |
| 7,959,675 B2 | 6/2011 | Gately | |
| 7,963,967 B1 | 6/2011 | Woods | |
| 7,967,863 B2 | 6/2011 | Frey et al. | |
| 7,976,566 B2 | 7/2011 | Michelson | |
| 7,981,156 B2 | 7/2011 | Pafford et al. | |
| 7,988,695 B2 | 8/2011 | Dye | |
| 7,988,699 B2 | 8/2011 | Martz et al. | |
| 7,993,347 B1 | 8/2011 | Michelson | |
| 7,998,209 B2 | 8/2011 | Branch et al. | |
| 7,998,215 B2 | 8/2011 | Frey et al. | |
| 8,007,535 B2 | 8/2011 | Hudgins et al. | |
| 8,012,212 B2 | 9/2011 | Link et al. | |
| 8,021,430 B2 | 9/2011 | Michelson | |
| 8,025,697 B2 | 9/2011 | McClellan, III et al. | |
| 8,034,110 B2 | 10/2011 | Garner et al. | |
| 8,038,703 B2 | 10/2011 | Dobak, III et al. | |
| 8,043,293 B2 * | 10/2011 | Warnick | A61F 2/4465 606/86 A |
| 8,048,159 B2 | 11/2011 | Ralph et al. | |
| 8,057,544 B2 | 11/2011 | Schaller | |
| 8,066,705 B2 | 11/2011 | Michelson | |
| 8,075,622 B2 | 12/2011 | Van Hoeck et al. | |
| 8,092,539 B2 | 1/2012 | Ralph et al. | |
| 8,092,568 B2 | 1/2012 | Konomi et al. | |
| 8,105,382 B2 | 1/2012 | Olmos et al. | |
| 8,128,700 B2 | 3/2012 | Delurio et al. | |
| 8,206,423 B2 | 6/2012 | Siegal | |
| 8,216,317 B2 | 7/2012 | Thibodeau | |
| 8,231,675 B2 | 7/2012 | Rhoda | |
| 8,241,364 B2 | 8/2012 | Hansell et al. | |
| 8,262,666 B2 | 9/2012 | Baynham et al. | |

(56) References Cited

U.S. PATENT DOCUMENTS

| | | |
|---|---|---|
| 8,267,939 B2 | 9/2012 | Cipoletti et al. |
| 8,292,959 B2 | 10/2012 | Webb et al. |
| 8,343,193 B2 | 1/2013 | Johnson et al. |
| 8,343,219 B2 | 1/2013 | Allain et al. |
| 8,343,222 B2 | 1/2013 | Cope |
| 8,366,777 B2 | 2/2013 | Matthis et al. |
| 8,372,084 B2 | 2/2013 | Pemsteiner et al. |
| 8,382,842 B2 | 2/2013 | Greenhalgh et al. |
| 8,394,109 B2 | 3/2013 | Hutton et al. |
| 8,403,990 B2 | 3/2013 | Dryer et al. |
| 8,409,292 B2 | 4/2013 | Michelson |
| 8,435,300 B2 | 5/2013 | Messerli et al. |
| 8,444,696 B2 | 5/2013 | Michelson |
| 8,454,617 B2 | 6/2013 | Schaller et al. |
| 8,469,960 B2 | 6/2013 | Hutton et al. |
| 8,480,745 B2 | 7/2013 | Liu et al. |
| 8,491,654 B2 | 7/2013 | Frey et al. |
| 8,506,629 B2 | 8/2013 | Weiland |
| 8,579,981 B2 | 11/2013 | Lim et al. |
| 8,597,356 B2 | 12/2013 | Rhoda |
| 8,628,577 B1 | 1/2014 | Jimenez |
| 8,663,331 B2 | 3/2014 | McClellan, III et al. |
| 8,690,949 B2 | 4/2014 | Messerli et al. |
| 8,734,447 B1 | 5/2014 | Michaelson |
| 8,758,344 B2 | 6/2014 | Michelson |
| 8,758,358 B2 | 6/2014 | Errico et al. |
| 8,845,733 B2 | 9/2014 | O'Neil et al. |
| 8,845,734 B2 | 9/2014 | Weiman |
| 8,858,564 B2 | 10/2014 | Errico et al. |
| 8,858,638 B2 | 10/2014 | Michelson |
| 8,882,661 B2 | 11/2014 | Hutton et al. |
| 8,911,442 B2 | 12/2014 | Wing et al. |
| 8,920,506 B2 | 12/2014 | McGuckin, Jr. |
| 8,926,704 B2 | 1/2015 | Glerum et al. |
| 8,940,050 B2 | 1/2015 | Laurence et al. |
| 8,956,414 B2 | 2/2015 | Asaad |
| 8,961,609 B2 | 2/2015 | Schaller |
| 8,968,408 B2 | 3/2015 | Schaller et al. |
| 8,986,389 B2 | 3/2015 | Lim et al. |
| 9,023,109 B2 | 5/2015 | Weiland |
| 9,028,553 B2 * | 5/2015 | Lindenmann ......... A61F 2/4684 623/17.16 |
| 9,101,488 B2 | 8/2015 | Malandain |
| 9,101,492 B2 | 8/2015 | Mangione et al. |
| 9,220,607 B2 | 12/2015 | Palmatier et al. |
| 9,332,750 B2 | 5/2016 | Mills et al. |
| 9,358,133 B2 | 6/2016 | Lindenmann et al. |
| 9,622,879 B2 | 4/2017 | Taylor et al. |
| 9,693,762 B2 | 7/2017 | Reimels |
| 9,844,400 B2 | 12/2017 | Stevenson et al. |
| 9,907,583 B2 | 3/2018 | Hayes |
| 10,070,971 B2 | 9/2018 | Palmatier et al. |
| 10,792,168 B2 | 10/2020 | Malcolmson et al. |
| 2002/0065560 A1 | 5/2002 | Varga et al. |
| 2002/0138078 A1 | 9/2002 | Chappuis |
| 2002/0138146 A1 | 9/2002 | Jackson |
| 2002/0143399 A1 | 10/2002 | Sutcliffe |
| 2002/0165550 A1 | 11/2002 | Frey |
| 2002/0165612 A1 | 11/2002 | Gerber et al. |
| 2002/0183758 A1 | 12/2002 | Middleton et al. |
| 2002/0193880 A1 | 12/2002 | Fraser |
| 2003/0023306 A1 | 1/2003 | Liu et al. |
| 2003/0028251 A1 | 2/2003 | Mathews |
| 2003/0060886 A1 | 3/2003 | Van Hoeck et al. |
| 2003/0065395 A1 | 4/2003 | Ralph et al. |
| 2003/0083747 A1 | 5/2003 | Winterbottom et al. |
| 2003/0093153 A1 | 5/2003 | Banick et al. |
| 2003/0135275 A1 | 7/2003 | Garcia et al. |
| 2003/0139812 A1 | 7/2003 | Garcia et al. |
| 2003/0139813 A1 | 7/2003 | Messerli et al. |
| 2003/0191531 A1 | 10/2003 | Berry et al. |
| 2003/0199881 A1 | 10/2003 | Bonutti |
| 2004/0002761 A1 | 1/2004 | Rogers et al. |
| 2004/0019356 A1 | 1/2004 | Fraser et al. |
| 2004/0030387 A1 | 2/2004 | Landry et al. |
| 2004/0034426 A1 | 2/2004 | Errico et al. |
| 2004/0038431 A1 | 2/2004 | Sluka et al. |
| 2004/0059337 A1 | 3/2004 | Hanson et al. |
| 2004/0059420 A1 | 3/2004 | Michelson |
| 2004/0068269 A1 | 4/2004 | Bonati et al. |
| 2004/0083000 A1 | 4/2004 | Keller et al. |
| 2004/0087947 A1 | 5/2004 | Lim et al. |
| 2004/0102784 A1 | 5/2004 | Pasquet et al. |
| 2004/0102846 A1 | 5/2004 | Keller et al. |
| 2004/0106996 A1 | 6/2004 | Liu et al. |
| 2004/0127990 A1 | 7/2004 | Bartish, Jr. et al. |
| 2004/0147129 A1 | 7/2004 | Rolfson |
| 2004/0153065 A1 | 8/2004 | Lim |
| 2004/0186574 A1 | 9/2004 | Varga et al. |
| 2004/0204714 A1 | 10/2004 | Liu et al. |
| 2004/0210308 A1 | 10/2004 | Carter et al. |
| 2004/0220668 A1 | 11/2004 | Eisermann et al. |
| 2004/0230306 A1 | 11/2004 | Hoeck et al. |
| 2005/0027360 A1 | 2/2005 | Webb et al. |
| 2005/0038431 A1 | 2/2005 | Bartish et al. |
| 2005/0096745 A1 | 5/2005 | Andre et al. |
| 2005/0107878 A1 | 5/2005 | Conchy |
| 2005/0119752 A1 | 6/2005 | Williams et al. |
| 2005/0149034 A1 | 7/2005 | Assell et al. |
| 2005/0165420 A1 | 7/2005 | Cha |
| 2005/0165484 A1 | 7/2005 | Ferree |
| 2005/0171541 A1 | 8/2005 | Boehm et al. |
| 2005/0177173 A1 | 8/2005 | Aebi et al. |
| 2005/0192241 A1 | 9/2005 | Banchereau et al. |
| 2005/0240193 A1 | 10/2005 | Layne et al. |
| 2006/0036244 A1 | 2/2006 | Spitler et al. |
| 2006/0058807 A1 | 3/2006 | Landry et al. |
| 2006/0064101 A1 | 3/2006 | Arramon |
| 2006/0064102 A1 | 3/2006 | Ebner |
| 2006/0069436 A1 | 3/2006 | Sutton et al. |
| 2006/0074429 A1 | 4/2006 | Ralph et al. |
| 2006/0100622 A1 | 5/2006 | Jackson |
| 2006/0100705 A1 | 5/2006 | Puno et al. |
| 2006/0106460 A1 | 5/2006 | Messerli et al. |
| 2006/0111715 A1 | 5/2006 | Jackson |
| 2006/0111728 A1 | 5/2006 | Abdou |
| 2006/0116767 A1 | 6/2006 | Magerl et al. |
| 2006/0122701 A1 | 6/2006 | Kiester |
| 2006/0129244 A1 | 6/2006 | Ensign |
| 2006/0142858 A1 | 6/2006 | Colleran et al. |
| 2006/0167547 A1 | 7/2006 | Suddaby |
| 2006/0189999 A1 | 8/2006 | Zwirkoski |
| 2006/0212118 A1 | 9/2006 | Abernathie |
| 2006/0229627 A1 | 10/2006 | Hunt et al. |
| 2006/0229724 A1 | 10/2006 | Lechmann et al. |
| 2006/0235426 A1 | 10/2006 | Lim et al. |
| 2006/0253120 A1 | 11/2006 | Anderson et al. |
| 2006/0254784 A1 | 11/2006 | Hartmann et al. |
| 2006/0265077 A1 | 11/2006 | Zwirkoski |
| 2006/0293753 A1 | 12/2006 | Thramann |
| 2007/0010885 A1 | 1/2007 | Liu et al. |
| 2007/0010886 A1 | 1/2007 | Banick et al. |
| 2007/0055264 A1 | 3/2007 | Parmigiani |
| 2007/0055272 A1 | 3/2007 | Schaller |
| 2007/0067035 A1 | 3/2007 | Falahee |
| 2007/0093897 A1 | 4/2007 | Gerbec et al. |
| 2007/0093901 A1 | 4/2007 | Grotz et al. |
| 2007/0118220 A1 | 5/2007 | Liu et al. |
| 2007/0142843 A1 | 6/2007 | Dye |
| 2007/0162132 A1 | 7/2007 | Messerli |
| 2007/0162138 A1 | 7/2007 | Heinz |
| 2007/0208343 A1 | 9/2007 | Magerl et al. |
| 2007/0213737 A1 | 9/2007 | Schermerhorn et al. |
| 2007/0213826 A1 | 9/2007 | Smith et al. |
| 2007/0225726 A1 | 9/2007 | Dye et al. |
| 2007/0225808 A1 | 9/2007 | Warnick |
| 2007/0225815 A1 | 9/2007 | Keith et al. |
| 2007/0233130 A1 | 10/2007 | Suddaby |
| 2007/0250167 A1 | 10/2007 | Bray et al. |
| 2007/0260314 A1 | 11/2007 | Biyani |
| 2007/0270957 A1 | 11/2007 | Heinz |
| 2007/0270968 A1 | 11/2007 | Baynham et al. |
| 2007/0282441 A1 | 12/2007 | Stream et al. |
| 2008/0009880 A1 | 1/2008 | Warnick et al. |

(56) References Cited

U.S. PATENT DOCUMENTS

| | | |
|---|---|---|
| 2008/0015701 A1 | 1/2008 | Garcia et al. |
| 2008/0027544 A1 | 1/2008 | Melkent |
| 2008/0027550 A1 | 1/2008 | Link et al. |
| 2008/0045966 A1 | 2/2008 | Buttermann et al. |
| 2008/0051890 A1 | 2/2008 | Waugh et al. |
| 2008/0058933 A1 | 3/2008 | Garner et al. |
| 2008/0065082 A1 | 3/2008 | Chang et al. |
| 2008/0077150 A1 | 3/2008 | Nguyen |
| 2008/0077153 A1 | 3/2008 | Pemsteiner et al. |
| 2008/0077241 A1 | 3/2008 | Nguyen |
| 2008/0077247 A1 | 3/2008 | Murillo et al. |
| 2008/0082173 A1 | 4/2008 | Delurio et al. |
| 2008/0091211 A1 | 4/2008 | Gately |
| 2008/0097454 A1 | 4/2008 | DeRidder et al. |
| 2008/0108990 A1 | 5/2008 | Mitchell et al. |
| 2008/0109083 A1 | 5/2008 | Van Hoeck et al. |
| 2008/0119935 A1 | 5/2008 | Alvarez |
| 2008/0125865 A1 | 5/2008 | Abdelgany |
| 2008/0133012 A1 | 6/2008 | McGuckin |
| 2008/0140085 A1 | 6/2008 | Gately et al. |
| 2008/0154379 A1 | 6/2008 | Steiner et al. |
| 2008/0172128 A1 | 7/2008 | Perez-Cruet et al. |
| 2008/0208255 A1 | 8/2008 | Siegal |
| 2008/0221586 A1 | 9/2008 | Garcia-Bengochea et al. |
| 2008/0221687 A1 | 9/2008 | Viker |
| 2008/0234732 A1 | 9/2008 | Landry et al. |
| 2008/0234733 A1 | 9/2008 | Scrantz et al. |
| 2008/0243126 A1 | 10/2008 | Gutierrez et al. |
| 2008/0243255 A1 | 10/2008 | Butler et al. |
| 2008/0249628 A1 | 10/2008 | Altarac et al. |
| 2008/0255563 A1 | 10/2008 | Farr et al. |
| 2008/0255574 A1 | 10/2008 | Dye |
| 2008/0269904 A1 | 10/2008 | Voorhies |
| 2008/0306488 A1 | 12/2008 | Altarac et al. |
| 2008/0312743 A1 | 12/2008 | Vila et al. |
| 2009/0030423 A1 | 1/2009 | Puno |
| 2009/0054898 A1 | 2/2009 | Gleason |
| 2009/0054911 A1 | 2/2009 | Mueller et al. |
| 2009/0062807 A1 | 3/2009 | Song |
| 2009/0076607 A1 | 3/2009 | Aalsma et al. |
| 2009/0088789 A1 | 4/2009 | O'Neil et al. |
| 2009/0105832 A1 | 4/2009 | Allain et al. |
| 2009/0112217 A1 | 4/2009 | Hester |
| 2009/0143859 A1 | 6/2009 | McClellan, III et al. |
| 2009/0164015 A1 | 6/2009 | Liu et al. |
| 2009/0182431 A1 | 7/2009 | Butler et al. |
| 2009/0192616 A1 | 7/2009 | Zielinski |
| 2009/0216234 A1 | 8/2009 | Farr et al. |
| 2009/0234364 A1 | 9/2009 | Crook |
| 2009/0240335 A1 | 9/2009 | Arcenio et al. |
| 2009/0276049 A1 | 11/2009 | Weiland |
| 2009/0299479 A1 | 12/2009 | Jones et al. |
| 2009/0317278 A1 | 12/2009 | Kokubo |
| 2010/0016968 A1 | 1/2010 | Moore |
| 2010/0030217 A1 | 2/2010 | Mitusina |
| 2010/0076502 A1 | 3/2010 | Guyer et al. |
| 2010/0094422 A1 | 4/2010 | Hansell et al. |
| 2010/0100098 A1 | 4/2010 | Norton et al. |
| 2010/0125334 A1 | 5/2010 | Krueger |
| 2010/0161060 A1 | 6/2010 | Schaller et al. |
| 2010/0174321 A1 | 7/2010 | Schaller |
| 2010/0185290 A1 | 7/2010 | Compton et al. |
| 2010/0191241 A1 | 7/2010 | McCormack et al. |
| 2010/0191337 A1 | 7/2010 | Zamani et al. |
| 2010/0198263 A1 | 8/2010 | Siegal et al. |
| 2010/0211076 A1 | 8/2010 | Germain et al. |
| 2010/0211107 A1 | 8/2010 | Muhanna |
| 2010/0217269 A1 | 8/2010 | Landes |
| 2010/0217394 A1 | 8/2010 | Michelson |
| 2010/0234849 A1 | 9/2010 | Bouadi |
| 2010/0249935 A1 | 9/2010 | Slivka et al. |
| 2010/0256768 A1 | 10/2010 | Lim et al. |
| 2010/0274358 A1 | 10/2010 | Mueller et al. |
| 2010/0280619 A1 | 11/2010 | Yuan et al. |
| 2010/0305700 A1 | 12/2010 | Ben-Arye et al. |
| 2010/0305704 A1 | 12/2010 | Messerli et al. |
| 2010/0331845 A1 | 12/2010 | Foley et al. |
| 2011/0004216 A1 | 1/2011 | Amendola et al. |
| 2011/0004314 A1 | 1/2011 | Baynham |
| 2011/0009970 A1 | 1/2011 | Puno |
| 2011/0029083 A1 | 2/2011 | Hynes et al. |
| 2011/0029085 A1 | 2/2011 | Hynes et al. |
| 2011/0035011 A1 | 2/2011 | Cain |
| 2011/0054529 A1 | 3/2011 | Michelson |
| 2011/0054621 A1 | 3/2011 | Lim |
| 2011/0093078 A1 | 4/2011 | Puno et al. |
| 2011/0106259 A1 | 5/2011 | Lindenmann et al. |
| 2011/0106260 A1 | 5/2011 | Laurence et al. |
| 2011/0112586 A1 | 5/2011 | Guyer et al. |
| 2011/0125266 A1 | 5/2011 | Rodgers et al. |
| 2011/0190891 A1 | 8/2011 | Suh et al. |
| 2011/0196501 A1 | 8/2011 | Michelson |
| 2011/0264218 A1 | 10/2011 | Asaad |
| 2011/0276142 A1 | 11/2011 | Niemiec et al. |
| 2011/0282459 A1 | 11/2011 | McClellan, III et al. |
| 2011/0301712 A1 | 12/2011 | Palmatier et al. |
| 2011/0319898 A1 | 12/2011 | O'Neil et al. |
| 2011/0319899 A1 | 12/2011 | O'Neil et al. |
| 2011/0319998 A1 | 12/2011 | O'Neil et al. |
| 2011/0319999 A1 | 12/2011 | O'Neil et al. |
| 2011/0320000 A1 | 12/2011 | O'Neil et al. |
| 2012/0023937 A1 | 2/2012 | Styles et al. |
| 2012/0035730 A1 | 2/2012 | Spann |
| 2012/0165943 A1 | 6/2012 | Mangione et al. |
| 2012/0209383 A1 | 8/2012 | Tsuang et al. |
| 2012/0277877 A1 | 11/2012 | Smith et al. |
| 2012/0310352 A1 | 12/2012 | DiMauro et al. |
| 2013/0006362 A1 | 1/2013 | Biedermann et al. |
| 2013/0023937 A1 | 1/2013 | Biedermann et al. |
| 2013/0035762 A1 | 2/2013 | Siegal et al. |
| 2013/0079790 A1 | 3/2013 | Stein et al. |
| 2013/0103102 A1 | 4/2013 | Taylor et al. |
| 2013/0109925 A1 | 5/2013 | Horton et al. |
| 2013/0110239 A1 | 5/2013 | Siegal et al. |
| 2013/0110241 A1 | 5/2013 | Palmatier et al. |
| 2013/0116791 A1 | 5/2013 | Theofilos |
| 2013/0138214 A1 | 5/2013 | Greenhalgh et al. |
| 2013/0150906 A1 | 6/2013 | Kerboul et al. |
| 2013/0173004 A1 | 7/2013 | Greenhalgh et al. |
| 2013/0190875 A1 | 7/2013 | Shulock et al. |
| 2013/0238006 A1 | 9/2013 | O'Neil et al. |
| 2013/0253652 A1 | 9/2013 | Michelson |
| 2013/0268077 A1 | 10/2013 | You et al. |
| 2013/0310937 A1 | 11/2013 | Pimenta |
| 2014/0025170 A1 | 1/2014 | Lim et al. |
| 2014/0039626 A1 | 2/2014 | Mitchell |
| 2014/0039627 A1 | 2/2014 | Weiland |
| 2014/0052259 A1 | 2/2014 | Garner et al. |
| 2014/0058512 A1 | 2/2014 | Petersheim |
| 2014/0058513 A1 | 2/2014 | Gahman et al. |
| 2014/0114413 A1 | 4/2014 | Allain et al. |
| 2014/0142704 A1 | 5/2014 | Ralph et al. |
| 2014/0172103 A1 | 6/2014 | O'Neil et al. |
| 2014/0172105 A1 | 6/2014 | Frasier et al. |
| 2014/0193798 A1 | 7/2014 | Mills et al. |
| 2015/0032212 A1 | 1/2015 | O'Neil et al. |
| 2015/0094812 A1 | 4/2015 | Cain |
| 2015/0150691 A1 | 6/2015 | Lim et al. |
| 2015/0196400 A1 | 7/2015 | Dace |
| 2015/0257898 A1 | 9/2015 | Weiland |
| 2016/0038306 A1 | 2/2016 | O'Neil et al. |
| 2016/0278937 A1 | 9/2016 | Weiland |
| 2018/0303624 A1 | 10/2018 | Shoshtaev |
| 2019/0038434 A1 | 2/2019 | Saito |

FOREIGN PATENT DOCUMENTS

| | | |
|---|---|---|
| DE | 19710392 C1 | 7/1999 |
| DE | 10241948 A1 | 4/2004 |
| DE | 10357960 B4 | 9/2015 |
| EP | 346129 A1 | 12/1989 |
| EP | 557686 A1 | 9/1993 |
| EP | 356112 B1 | 12/1993 |
| EP | 609084 A2 | 8/1994 |

(56) References Cited

FOREIGN PATENT DOCUMENTS

| | | |
|---|---|---|
| EP | 637439 A1 | 2/1995 |
| EP | 425542 B1 | 3/1995 |
| EP | 734702 A1 | 10/1996 |
| EP | 419564 B1 | 8/1998 |
| EP | 855886 A1 | 8/1998 |
| EP | 641547 B1 | 5/1999 |
| EP | 1092395 A2 | 4/2001 |
| EP | 1093760 A2 | 4/2001 |
| EP | 720455 B1 | 1/2002 |
| EP | 712607 B1 | 2/2002 |
| EP | 615428 B1 | 3/2002 |
| EP | 752830 B1 | 6/2002 |
| EP | 1222898 A3 | 8/2002 |
| EP | 1265562 A2 | 12/2002 |
| EP | 916323 B1 | 1/2003 |
| EP | 1283026 A2 | 2/2003 |
| EP | 1290985 A2 | 3/2003 |
| EP | 1294321 A1 | 3/2003 |
| EP | 836455 B1 | 4/2003 |
| EP | 812167 B1 | 5/2003 |
| EP | 1308132 A2 | 5/2003 |
| EP | 703757 B1 | 8/2003 |
| EP | 855887 B1 | 8/2003 |
| EP | 1221914 B1 | 9/2003 |
| EP | 1219248 A3 | 1/2004 |
| EP | 1219268 A3 | 1/2004 |
| EP | 1344509 A3 | 2/2004 |
| EP | 1391188 A1 | 2/2004 |
| EP | 831759 B1 | 3/2004 |
| EP | 1405602 A1 | 4/2004 |
| EP | 1129668 B1 | 5/2004 |
| EP | 901351 B1 | 8/2004 |
| EP | 836457 B1 | 9/2004 |
| EP | 732093 B1 | 11/2004 |
| EP | 814718 B1 | 11/2004 |
| EP | 1197181 B1 | 11/2004 |
| EP | 1124510 B1 | 12/2004 |
| EP | 1488755 A1 | 12/2004 |
| EP | 1508307 A1 | 2/2005 |
| EP | 988003 B1 | 5/2005 |
| EP | 1346695 B1 | 12/2005 |
| EP | 1605836 A1 | 12/2005 |
| EP | 1221915 B1 | 2/2006 |
| EP | 1389983 B1 | 8/2006 |
| EP | 1684675 A1 | 8/2006 |
| EP | 1009338 B1 | 10/2006 |
| EP | 1709920 A3 | 10/2006 |
| EP | 1722722 A1 | 11/2006 |
| EP | 1374806 B1 | 12/2006 |
| EP | 1525863 A3 | 1/2007 |
| EP | 1762202 A2 | 3/2007 |
| EP | 1764066 A1 | 3/2007 |
| EP | 840580 B1 | 4/2007 |
| EP | 1009337 B1 | 6/2007 |
| EP | 1514519 A3 | 7/2007 |
| EP | 1618848 B1 | 7/2007 |
| EP | 1442732 B1 | 9/2007 |
| EP | 1829486 A1 | 9/2007 |
| EP | 1841385 A1 | 10/2007 |
| EP | 1153574 B1 | 2/2008 |
| EP | 1905390 A2 | 4/2008 |
| EP | 1905391 A1 | 4/2008 |
| EP | 1302182 B1 | 8/2008 |
| EP | 1437105 B1 | 10/2008 |
| EP | 1905931 B1 | 12/2008 |
| EP | 2016924 A3 | 4/2009 |
| EP | 2058014 A1 | 5/2009 |
| EP | 1829503 B1 | 9/2009 |
| EP | 1383449 B1 | 11/2009 |
| EP | 1439773 B1 | 1/2010 |
| EP | 1437988 B1 | 3/2010 |
| EP | 1500372 B1 | 3/2010 |
| EP | 1596764 B1 | 3/2010 |
| EP | 1549259 B1 | 4/2010 |
| EP | 1400221 B1 | 9/2011 |
| EP | 1833428 B1 | 4/2012 |
| EP | 1653892 B1 | 4/2013 |
| FR | 2703580 A1 | 10/1994 |
| FR | 2736537 A1 | 1/1997 |
| FR | 2738475 A1 | 3/1997 |
| FR | 2817463 A1 | 6/2002 |
| FR | 2841125 A1 | 12/2003 |
| FR | 2874814 A1 | 3/2006 |
| FR | 2948277 A1 | 1/2011 |
| JP | 2006-508714 A | 3/2006 |
| JP | 2006-516456 A | 7/2006 |
| JP | 2007-501027 A | 1/2007 |
| JP | 2007-517539 A | 7/2007 |
| JP | 2010-538683 A | 12/2010 |
| WO | 89/09035 A1 | 10/1989 |
| WO | 90/00037 A1 | 1/1990 |
| WO | 92/014423 A1 | 9/1992 |
| WO | 93/01771 A1 | 2/1993 |
| WO | 95/08964 A2 | 4/1995 |
| WO | 95/15133 A1 | 6/1995 |
| WO | 95/20370 A1 | 8/1995 |
| WO | 95/26164 A1 | 10/1995 |
| WO | 95/32673 A1 | 12/1995 |
| WO | 96/27321 A2 | 9/1996 |
| WO | 96/27345 A2 | 9/1996 |
| WO | 96/39988 A2 | 12/1996 |
| WO | 96/40015 A1 | 12/1996 |
| WO | 96/40019 A1 | 12/1996 |
| WO | 96/400520 A1 | 12/1996 |
| WO | 97/14377 A1 | 4/1997 |
| WO | 97/20526 A1 | 6/1997 |
| WO | 97/37620 A1 | 10/1997 |
| WO | 98/01091 A1 | 1/1998 |
| WO | 98/17208 A1 | 4/1998 |
| WO | 98/034568 A1 | 8/1998 |
| WO | 98/56319 A1 | 12/1998 |
| WO | 99/09896 A1 | 3/1999 |
| WO | 99/09913 A2 | 3/1999 |
| WO | 99/060956 A1 | 12/1999 |
| WO | 99/063914 A1 | 12/1999 |
| WO | 00/24343 A1 | 5/2000 |
| WO | 0024327 A2 | 5/2000 |
| WO | 00/74605 A1 | 12/2000 |
| WO | 01/28465 A2 | 4/2001 |
| WO | 01/68005 A2 | 9/2001 |
| WO | 01/95838 A1 | 12/2001 |
| WO | 2002/003870 A1 | 1/2002 |
| WO | 02/17823 A1 | 3/2002 |
| WO | 2003/003951 A1 | 1/2003 |
| WO | 03/32802 A2 | 4/2003 |
| WO | 2004/000176 A1 | 12/2003 |
| WO | 2004/000177 A1 | 12/2003 |
| WO | 2004/069033 A2 | 8/2004 |
| WO | 2004/080316 A1 | 9/2004 |
| WO | 2005/011539 A2 | 2/2005 |
| WO | 2005/041825 A1 | 5/2005 |
| WO | 2005/087143 A1 | 9/2005 |
| WO | 2005/094297 A2 | 10/2005 |
| WO | 2006/044920 A2 | 4/2006 |
| WO | 2006/072941 A2 | 7/2006 |
| WO | 2006/079356 A1 | 8/2006 |
| WO | 2006/118944 A1 | 11/2006 |
| WO | 2007/016801 A1 | 2/2007 |
| WO | 2007/048012 A2 | 4/2007 |
| WO | 2007/070751 A2 | 6/2007 |
| WO | 2007/093900 A2 | 8/2007 |
| WO | 2008/036636 A2 | 3/2008 |
| WO | 2008/079953 A3 | 10/2008 |
| WO | 2010/011348 A1 | 1/2010 |
| WO | 2010/075555 A2 | 7/2010 |
| WO | 2010/121002 A1 | 10/2010 |
| WO | 2011/013047 A2 | 2/2011 |
| WO | 2011/056172 A1 | 5/2011 |
| WO | 2011/060087 A1 | 5/2011 |
| WO | 2012/027490 A2 | 3/2012 |
| WO | 2012103254 A2 | 8/2012 |
| WO | 2012/129197 A1 | 9/2012 |
| WO | 2013/149611 A1 | 10/2013 |

(56) References Cited

FOREIGN PATENT DOCUMENTS

OTHER PUBLICATIONS

Al-Sanabani, Application of Calcium Phosphate Materials in Dentistry, vol. 2013, Int. J. Biomaterials, Jan. 12, 2013.
Bailey, Stabilzation of the Cervical Spine by Anterior Fusion, 42-A(4), J. Bone Joint Surg., 565-594, Jun. 1960.
Banward, Iliac Crest Bone Graft Harvest Donor Site Morbidity, 20(9) Spine 1055-1060, May 1995.
Benezech, L'arthrodese Cervicale Par Voie Anterieure a L'Aide de Plaque-Cage P.C.B., 9(1) Rachis 1, 47, 1997 (w/Translation).
Brantigan 1/F Cage for PLIF Surgical Technique Guide; Apr. 1991, 22 pages.
Brantigan, A Carbon Fiber Implant to Aid Interbody Lumbar Fusion, 16(6S) Spine S277-S282, Jul. 1991.
Brantigan, Compression Strength of Donor Bone for Posterior Lumbar Interbody Fusion, 18(9) Spine 1213-1221, 1993.
Brantigan, Interbody Lumbar Fusion Using a Carbon Fiber Cage Implant Versus Allograft Bone, 19(13) Spine 1436-1444, 1994.
Brantigan, Intervertebral Fusion, Chapter 27, Posterior Lumbar Interbody Fusion Using the Lumbar Interbody Fusion Cage, 437-466, 2006.
Brantigan, Pseudarthrosis Rate After Allograft Posterior Lumbar Interbody Fusion with Pedicle Screw and Plate Fixation, 19(11) Spine 1271-1280, Jun. 1994.
Carbon Fiber Composite Ramps for Lumbar Interbody Fusion; Apr. 1997, 2 pages.
Cloward, Gas-Sterilized Cadaver Bone Grafts for Spinal Fusion Operations, 5(1) Spine 4-10 Jan./Feb. 1980.
Cloward, The Anterior Approach for Removal of Ruptured Cervical Disks, vol. 15, J. Neuro. 602-617, 1958.
Dabrowski, Highly Porous Titanium Scaffolds for Orthopaedic Applications, J. Biomed Mater. Res. B. Appl. Biomat. Oct;95(1):53-61, 2010.
Delecrin, Morbidite du Prelevement de Greffons osseuz au Niveau des Cretes Iliaques dans la Chirurgie Du Rachis; Justification du recours aux substituts osseuz, 13(3) Rachis 167-174, 2001 (w/Translation).
DePuy Motech Surgical Titanium Mesh Brochure; 1998, 13 pages.
Dereymaeker, Nouvelle Cure neuro-Chirurgicale de discopathies Cervicales, 2 Neurochirurgie 226-234; 1956 (w/Translation).
Dickman, Internal Fixation and Fusion of the Lumbar Spine Using Threaded Interbody Cages, 13(3) Barrow Quarterly (1997); http://www.thebarrow.org/Education_And_Resources/Barrow_Quarterly/204837.
Enker, Interbody Fusion and Instrumentation, No. 300 Clin. Orth. Rel. Res. 90-101, Mar. 1994.
Fassio, Use of Cervical Plate-Cage PCB and Results for Anterior Fusion in Cervical Disk Syndrome, 15(6) Rachis 355-361, Dec. 2003 Translation.
Fowler, Complications Associated with Harvesting Autogenous Iliac Bone Graft, 24(12) Am. J. Ortho. 895-904, Dec. 1995.
Fuentes, Les Complications de la Chirurgie Par Voie Anterieure du Rachis Cervical, 8(1) Rachis 3-14, 1996 (w/Translation).
Germay, Resultats Cliniques de Ceramiques D'hydroxyapatite dans les arthrodeses Inter-somatiques du Rachis Cervical Par Voie Anterieure. Etude Retrospective a Propose de 67 cas. 13(3), Rachis 189-195, 2001 (w/Translation).
Graham, Lateral Extracavitary Approach to the Thoracic and Thoracolumbar Spine, 20(7) Orthopedics, 605-610, Jul. 1997.
Gunatillake, Biodegradable Synthetic Polymers for Tissue Engineering, vol. 5, Eur. Cells Materials, Jan. 16, 2003.
Huttner, Spinal Stenosis & Posterior Lumbar Interbody Fusion, No. 193, Clinical Ortho Rel. Res. 103-114, Mar. 1985.
Jost, Compressive Strength of Interbody Cages in the Lumbar Spine: the Effect of Cage Shape, Posterior Instrumentation and Bone Density, 7 Eur. Spine J. 132-141, 1998.
Kastner, Advanced X-Ray Tomographic Methods for Quantitative Charecterisation of Carbon Fibre Reinforced Polymers, 4th Annual Intern. Symposium on NDT in Aerospace, 2012, 9 pages.

Khan, Chapter 2—Implantable Medical Devices, Focal Controlled Drug Delivery, Advances in Delivery Science and Technology, A.J. Domb and W. Khan (eds.) 2014.
Kozak, Anterior Lumbar Fusion Options, No. 300, Clin. Orth. Rel. Res., 45-51, 1994.
Kroppenstedt, Radiological Comparison of Instrumented Posterior Lumbar Interbody Fusion with One or Two Closed-Box Plasmapore Coated Titanium Cages, 33(19) Spine, 2083-2088, Sep. 2008.
Lund, Interbody Cage Stabilisation in the Lumbar Spine, 80(2) J Bone Joint Surg., 351-359, Mar. 1998.
Lyu, Degradability of Polymers for Implantable Biomedical Devices, 10, Int. J. Mal. Sci., 4033-4065, 2009.
Malca, Cervical Interbody Xenograft with Plate Fixation, 21(6) Spine, 685-690, Mar. 1996.
McAfee, Minimally Invasive Anterior Retroperitoneal Approach to the Lumbar Spine, 21(13) Spine, 1476-1484, 1998.
Nasca, Newer Lumbar Interbody Fusion Techniques, 22(2) J. Surg. Ortho. Advances, 113-117,2013.
PCB Evolution Surgical Technique Guide 2010.
Polysciences Inc. Info Sheet 2012.
Porex Website, http://www.porex.com/technologies/materials/porous-plastics, Porous Plastic Materials, accessed Aug. 21, 2015, 2 pages.
Samandouras, A New Anterior Cervical Instrumentation System Combining an Intradiscal Cage with an Integrated Plate, 26(10) Spine, 1188-1192, 2001.
Sonntag, Controversy in Spine Care, Is Fusion Necessary After Anterior Cervical Discectomy 21(9) Spine, 1111-1113, May 1996.
Supplementary EP Search Report for European Application 00980805 (EP1239796A4) dated Feb. 26, 2007, 3 pages.
Supplementary EP Search Report for European Application 01908625 (EP1416891A4) dated Dec. 15, 2006, 4 pages.
Supplementary EP Search Report for European Application 03749686 (EP1555966A4) dated Feb. 3, 2011, 3 pages.
Supplementary EP Search Report for European Application 03752374 (EP1549259A4) dated Mar. 20, 2007, 4 pages.
Supplementary EP Search Report for European Application 03786692 (EP1570222A4) dated Sep. 19, 2008, 2 pages.
Supplementary EP Search Report for European Application 03813779 (EP1587460A4) dated Nov. 4, 2010, 4 pages.
Synthes History and Evolution of LBIF Brochure; Nov. 2015, 30 pages.
Synthes Spine Cervical Stand-Alone Devices Presentation Brochure; 2010, 40 pages.
U.S. Appl. No. 16/037,168, filed Jul. 17, 2018, Implant Inserters and Related Methods.
Synthes Spine, "OPAL Spacer System. Oblique posterior atraumatic lumbar spacer system, Technique Guide" (Brochure), 2008, US.
Synthes Spine, "T-PLIF Spacer Instruments, Technique Guide", (Brochure), 2001, US.
Synthes Spine, "Vertebral Spacer-TR" (Brochure), 2002, US.
Synthes Spine, "Vertebral Spacer-PR", (Brochure), 2002, US.
Synthes Spine, "Vertebral Spacer-PR. Vertebral body replacement device intended for use in the thoracolumbar spine", (Brochure), 2002, US.
Takahama, A New Improved Biodegradable Tracheal Prosthesis Using Hydroxy Apatite and Carbon Fiber 35(3) ASAIO Trans, 291-293, Jul.-Sep. 1989.
Tamariz, Biodegradation of Medical Purpose Polymeric Materials and Their Impact on Biocompatibility, Chapter 1, Intech-bio degradation Life of Science, 2013; 28 pages.
Tan, A Modified Technique of Anterior Lumbar Fusion with Femoral Cortical Allograft, 5(3) J. Ortho. Surg. Tech., 83-93, 1990.
Verbiest H., La Chirurgie Anterieure et Laterale du Rachis Cervical,16(S2) Neurochirurgie 1-212; 1970 (w/Translation).
Wang, Determination of Cortical Bone Porosity and Pore Size Distribution using a Low Field Pulsed NMR Approach, J. Orthop Res., Mar; 21(2):312-9 Mar. 2003.
Wang, Increased Fusion Rates with Cervical Plating for Two-Level Anterior Cervical Discectomy and Fusion, 25(1) Spine 41-45, Jan. 2000.
Watters, Anterior Cervical Discectomy with and without Fusion, 19(20) Spine 2343-2347 Oct. 1994.

(56) References Cited

OTHER PUBLICATIONS

Weiner, Spinde Update Lumbar Interbody Cages, 23(5) Spine, 634-640, Mar. 1998.
White, Relief of Pain by Anterior Cervical-Spine Fusion for Spondylosis, 55-A(3) J. Bone Joint Surg. 525-534, Apr. 1973.
Whitesides, Lateral Approach to the Upper Cervical Spine for Anterior Fusion, vol. 59, South Med J, 879-883, Aug. 1966.
Wilson, Anterior Cervical Discectomy without Bone Graft, 47(4) J. Neurosurg. 551-555, Oct. 1977.
Younger, Morbidity at Bone Graft Donor Sites, 3(3) J. Orth. Trauma, 192-195, 1989.

* cited by examiner

INTERVERTEBRAL IMPLANT INSERTERS AND RELATED METHODS

CROSS-REFERENCE TO RELATED APPLICATIONS

This application claims the benefit of U.S. Provisional Application No. 62/544,997, filed Aug. 14, 2017, the entire contents of which are incorporated herein by reference.

FIELD

Implant inserters and related methods are disclosed herein, e.g., for delivering a fusion cage or other implant to a spinal disc space and for rotating or articulating the implant within the disc space.

BACKGROUND

There are a number of surgical procedures in which an implant is delivered to a location within a patient. In spine surgery, for example, a fusion cage, disc prosthesis, or other implant may be delivered to a disc space defined between two vertebrae. Insertion and proper positioning of the implant can be challenging for the surgeon, particularly when the implant is delivered through a narrow working channel, e.g., in the case of minimally-invasive approaches to the spine.

By way of further example, in some spinal surgeries, a relatively medial posterior approach to an intervertebral disc space can be desired because the degree of muscle stripping and soft tissue retraction required to access the disc space can be reduced relative to other approaches. In such cases, however, any instruments passed to the surgical site can come close to the spinal cord. With prior devices, such an approach can be impractical or impossible due to the device being too large to pass into the disc space without undesirably contacting sensitive anatomic structures like the spinal cord.

Accordingly, there is a need for improved instruments having reduced profile geometries to allow insertion through narrow passages or working channels. In particular, there is a need for improved implant inserters and related methods that can facilitate insertion and proper positioning of an implant within a patient.

SUMMARY

Implant inserters and related methods are disclosed herein, e.g., for delivering a fusion cage or other implant to a spinal disc space and for rotating or articulating the implant within the disc space. An exemplary instrument can include an inner member having opposed jaws for grasping the implant and holding the implant during insertion. The inner member can be slidably received within an outer member such that relative axial translation of the inner and outer members is effective to open or close the jaws. The jaws and/or the distal end of the outer member can have a low-profile geometry, which can advantageously facilitate certain surgical procedures. For example, the low-profile geometry can allow for a more medial approach to an intervertebral disc space in which the implant is to be inserted.

In one aspect, a surgical instrument is provided that can include an outer member having a central longitudinal axis and an inner member having a medial jaw and a lateral jaw. Further, the inner member can be axially translatable within an inner passage of the outer member to move the jaws towards one another to a closed position, thereby grasping an implant. Still further, at least one of the following conditions can be true when the jaws are in the closed position: the medial jaw can have a length that is less than a length of the lateral jaw; the medial jaw can have a knuckle width that is less than a knuckle width of the lateral jaw; the medial jaw can be asymmetrical to the lateral jaw; a claw opening distance between the medial and lateral jaws can be oriented at an oblique angle with respect to the central longitudinal axis of the outer member; the distal end of the outer member can have a width that is less than a maximum outer width of the medial and lateral jaws; the distance between the maximum lateral extent of the lateral jaw and the central longitudinal axis of the outer member can be greater than the distance between the maximum medial extent of the medial jaw and the central longitudinal axis of the outer member; a maximum medial extent of the medial jaw can be less than or equal to a maximum medial extent of the outer member; and a maximum medial extent of the medial jaw can be less than or equal to a maximum medial extent of an implant loaded into the instrument.

In another aspect, a surgical instrument is provided that can include an outer member having a central longitudinal axis and an inner member having a medial jaw and a lateral jaw. Further, the inner member can be axially translatable within an inner passage of the outer member to move the jaws towards one another to a closed position, thereby grasping an implant.

The devices and methods described herein can have a number of additional features and/or variations, all of which are within the scope of the present disclosure. In some embodiments, for example, the medial jaw can have a length that is less than a length of the lateral jaw when the jaws are in the closed position.

In certain embodiments, the medial jaw can have a knuckle width that is less than a knuckle width of the lateral jaw. And in some embodiments, the medial jaw can be asymmetrical to the lateral jaw. Further, in some embodiments a claw opening distance between the medial and lateral jaws can be oriented at an oblique angle with respect to the central longitudinal axis of the outer member.

In some embodiments, the distal end of the outer member can have a width that is less than a maximum outer width of the medial and lateral jaws when the jaws are in the closed position. And in certain embodiments, the distance between the maximum lateral extent of the lateral jaw and the central longitudinal axis of the outer member can be greater than the distance between the maximum medial extent of the medial jaw and the central longitudinal axis of the outer member when the jaws are in the closed position.

In certain embodiments, a maximum medial extent of the medial jaw can be less than or equal to a maximum medial extent of the outer member when the jaws are in the closed position. While in some embodiments, a maximum medial extent of the medial jaw can be less than or equal to a maximum medial extent of an implant loaded into the instrument when the jaws are in the closed position.

In some embodiments, the instrument can further include an implant grasped between the medial and lateral jaws of the inner member, and the medial jaw does not protrude or overhang the implant in the medial direction.

In another aspect, a surgical method is provided that can include coupling an implant to an inserter such that the inserter does not protrude or overhang the implant on at least a first side thereof, passing the implant into a disc space between two vertebrae such that the first side faces in the medial direction, and releasing the implant from the inserter.

As with the above-described aspect, a number of additional features and/or variations can be included, all of which are within the scope of the present disclosure. In some embodiments, for example, coupling the implant to the inserter can include passing a portion of the implant into an opening between two jaws of the inserter and moving the two jaws toward one another to clamp the implant. And in certain embodiments, moving the two jaws toward one another can include distally advancing an outer member relative to an inner member on which the two jaws are formed. Further, in some embodiments releasing the implant from the inserter can include proximally withdrawing the outer member relative to the inner member.

The method can be used in a variety of procedures. For example, in certain embodiments passing the implant into the disc space can be done using any of a PLIF approach, a TLIF approach, a medially-shifted PLIF approach, and a medially-shifted TLIF approach.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The aspects and embodiments described above will be more fully understood from the following detailed description taken in conjunction with the accompanying drawings, in which.

DETAILED DESCRIPTION

Implant inserters and related methods are disclosed herein, e.g., for delivering a fusion cage or other implant to a spinal disc space and for rotating or articulating the implant within the disc space. An exemplary instrument can include an inner member having opposed jaws for grasping the implant and holding the implant during insertion. The inner member can be slidably received within an outer member such that relative axial translation of the inner and outer members is effective to open or close the jaws. The jaws and/or the distal end of the outer member can have a low-profile geometry, which can advantageously facilitate certain surgical procedures. For example, the low-profile geometry can allow for a more medial approach to an intervertebral disc space in which the implant is to be inserted.

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments and methods specifically described herein and illustrated in the accompanying drawings are non-limiting exemplary embodiments. The features illustrated or described in connection with one exemplary embodiment may be combined with the features of other embodiments.

Figure 1:
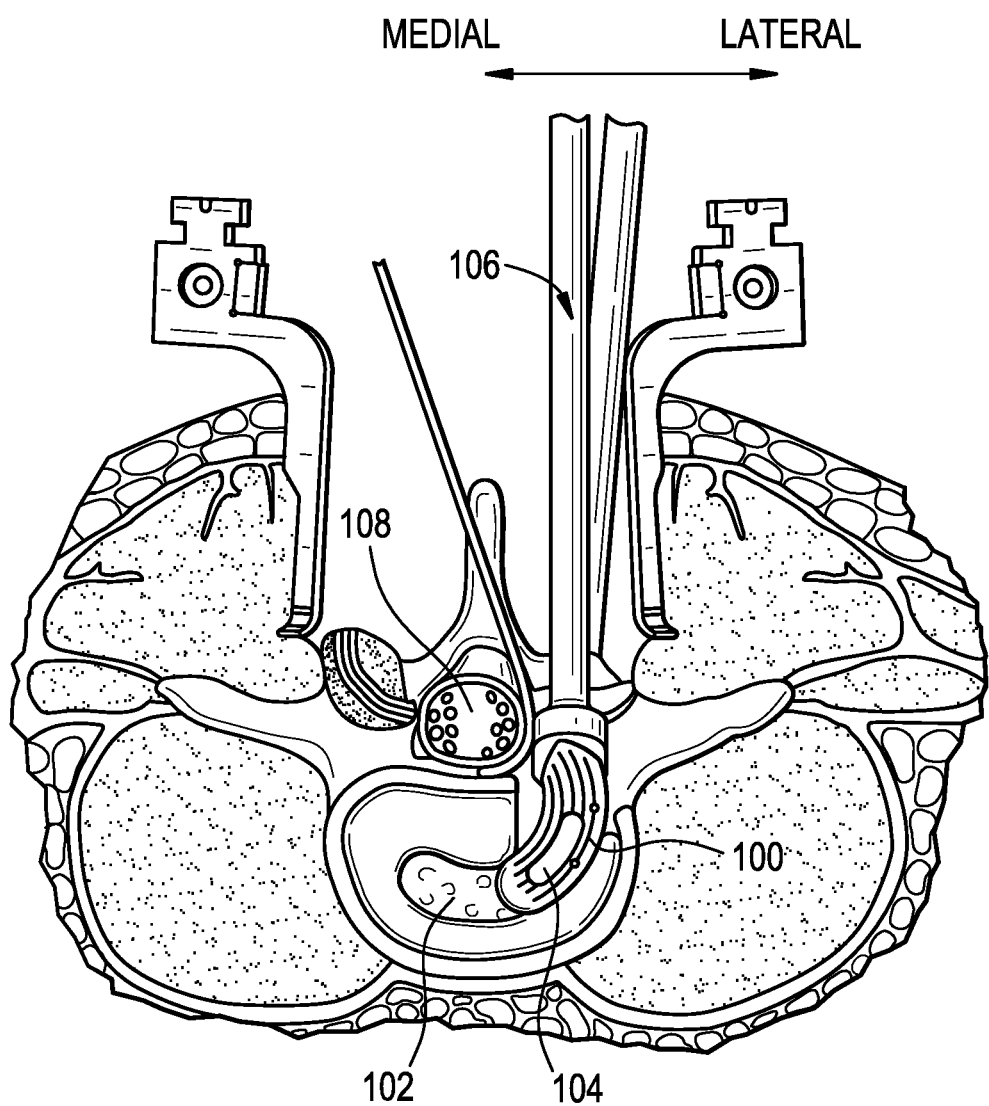
FIG. 1 is a transverse plane sectional view of a human spine, showing an instrument being used to insert an implant into an intervertebral disc space.

FIG. 1 illustrates an exemplary spinal surgical procedure in which an implant 100 is inserted into an intervertebral disc space 102. The implant 100 can be a fusion cage designed to promote fusion between vertebrae above and below the disc space 102. The fusion cage 100 and/or the disc space 102 surrounding the cage can be packed with bone graft material 104 or other fusion-promoting substances. In other embodiments, the implant 100 can be a disc prosthesis, motion preserving implant, or the like. The implant 100 can be delivered to the disc space 102 using an inserter instrument 106. The implant 100 can be delivered using any of a variety of approaches to the intervertebral disc space 102, with each approach having certain potential advantages and/or disadvantages. One advantage of a relatively medial posterior approach to the disc space 102 is that the degree of muscle stripping and soft tissue retraction required to access the disc space may be reduced as compared to more lateral approaches. As shown in FIG. 1, the degree to which an approach can be shifted in the medial direction is limited by the location of the spinal cord 108 and/or other delicate anatomical structures. When a relatively medial posterior approach is used to access the disc space 102, the inserter instrument 106 must pass very close to the spinal cord 108. By reducing the profile of the inserter instrument 106, and in particular the medial aspects of the inserter instrument, the implant 100 can be inserted along a path that is more medial and thus potentially less invasive.

Figure 2A:
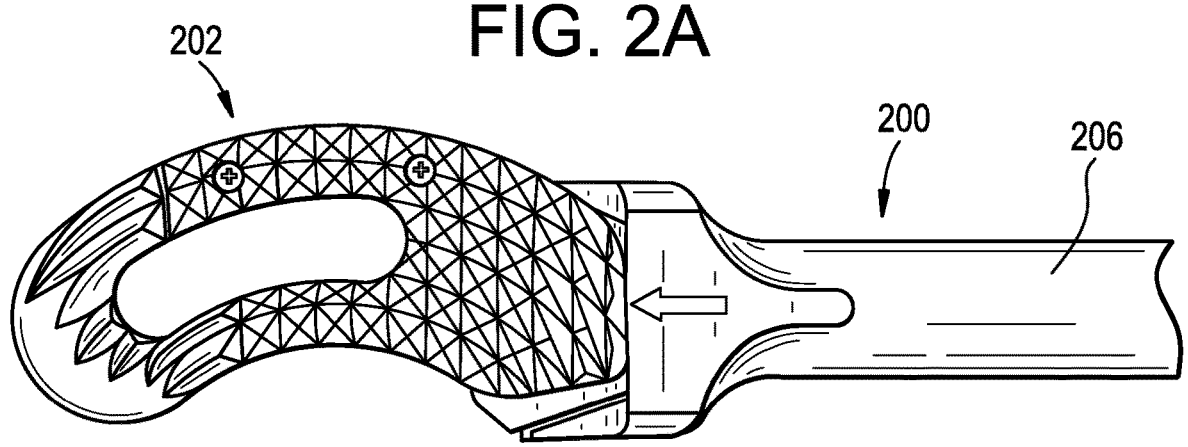
FIG. 2A is a top view of a predicate implant inserter, shown with an implant loaded into the inserter.
Figure 2B:
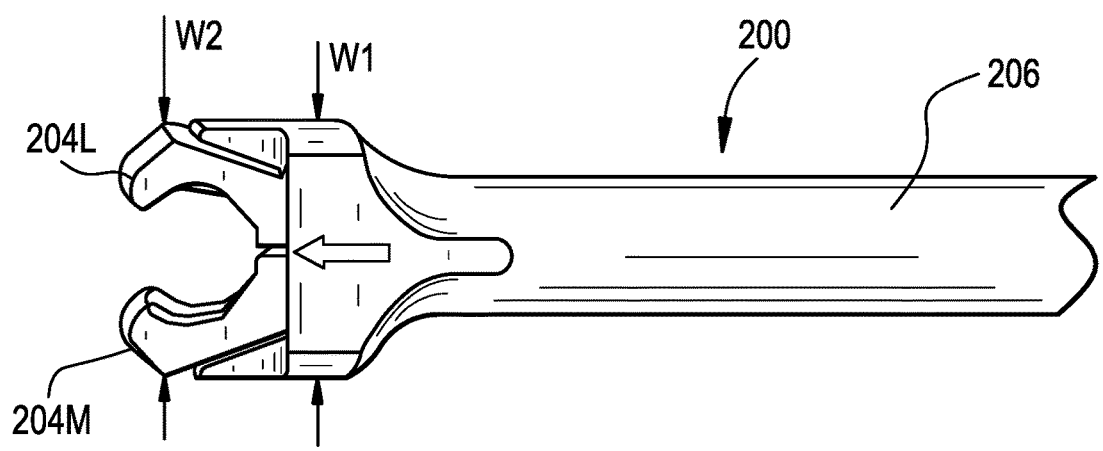
FIG. 2B is a top view of the predicate implant inserter of FIG. 2A, shown in an unloaded configuration.

FIGS. 2A and 2B illustrate a predicate inserter instrument 200 shown with an implant 202 loaded into the inserter (FIG. 2A) and unloaded (FIG. 2B). Further details on the inserter instrument 200 and the implant 202 can be found in U.S. Publication No. 2011/0106259 entitled "SELF-PIVOTING SPINAL IMPLANT AND ASSOCIATED INSTRUMENTATION," which is hereby incorporated by reference herein. The inserter instrument 200 has an inner member with opposed medial and lateral jaws 204M, 204L for grasping the implant 202. The inner member is slidably received within an outer member 206 such that relative axial translation of the inner and outer members is effective to open or close the jaws 204. As shown, the jaws 204 are symmetrical to one another, i.e., such that each jaw has a shape that is the same but opposite that of the other jaw. In addition, the distal end of the outer member 206 has a width W1 that is relatively wide, the width W1 being equal to or greater than the maximum outer width W2 of the jaws 204. In use, the inserter instrument 200 is guided towards the disc space with the width dimensions W1, W2 oriented along the transverse plane. The geometry of the jaws 204 and/or of the distal end of the outer member 206 can limit the degree to which an approach to the disc space can be shifted medially.

Figure 3A:
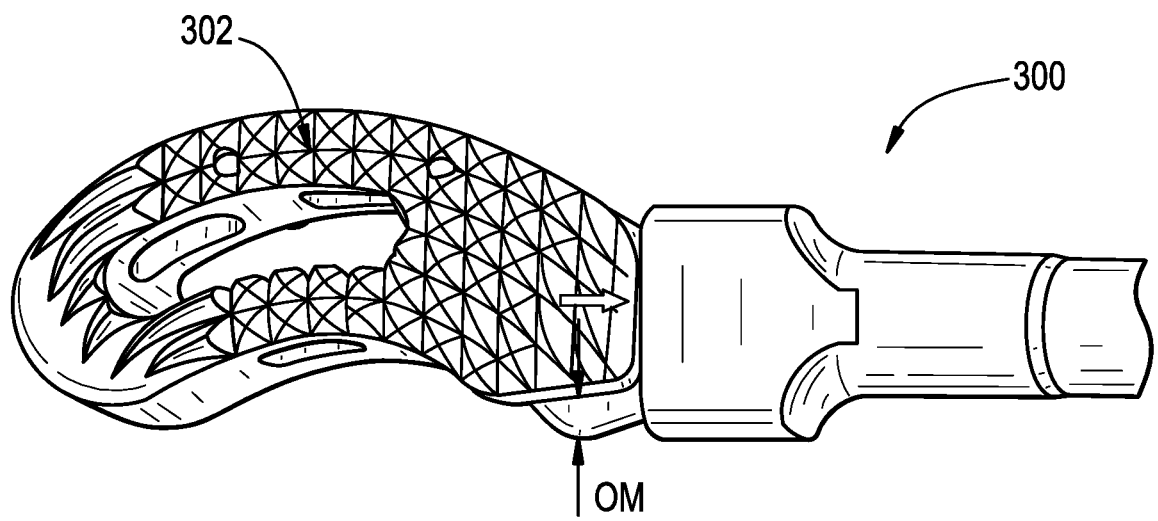
FIG. 3A is a top view of an implant inserter in accordance with the present disclosure, shown with an implant loaded into the inserter.
Figure 3B:
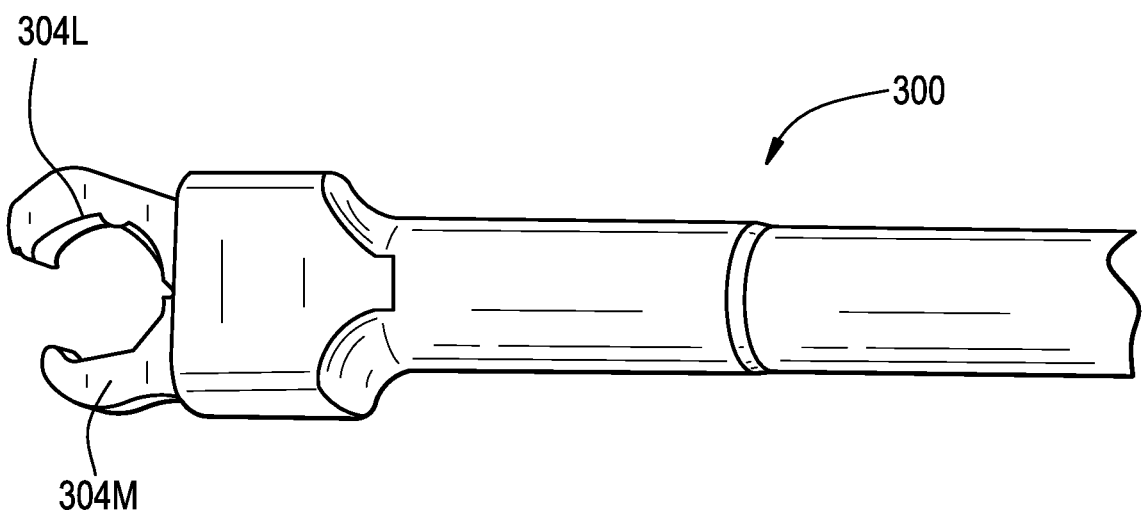
FIG. 3B is a top view of the implant inserter of FIG. 3A, shown in an unloaded configuration.
Figure 3C:
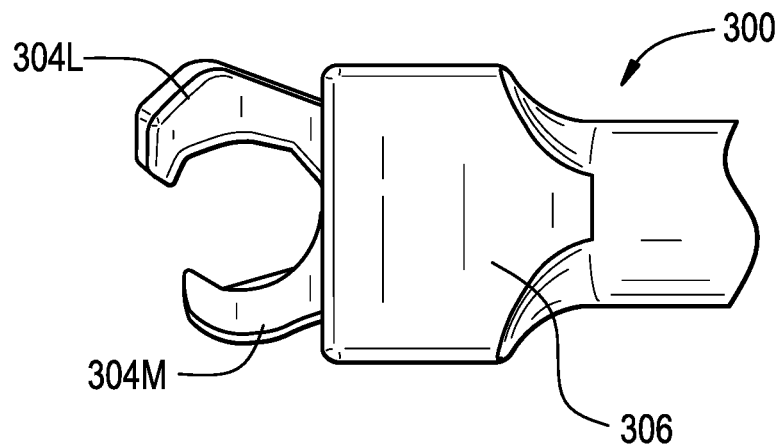
FIG. 3C is a top view of the implant inserter of FIG. 3A, shown in a closed position.
Figure 3D:
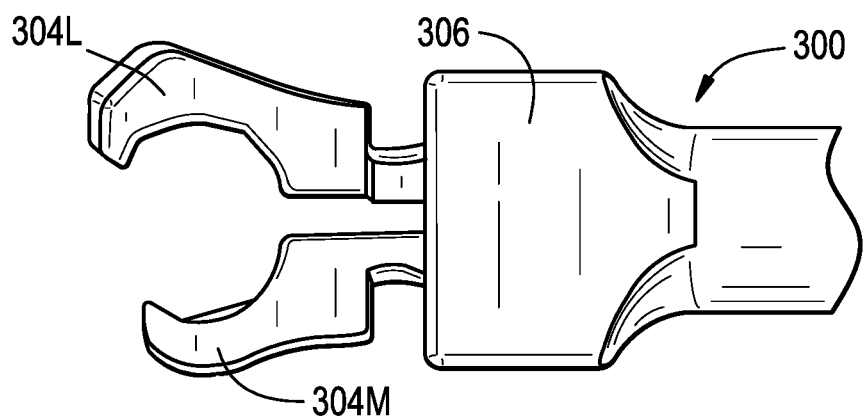
FIG. 3D is a top view of the implant inserter of FIG. 3A, shown in an open position.
Figure 3E:
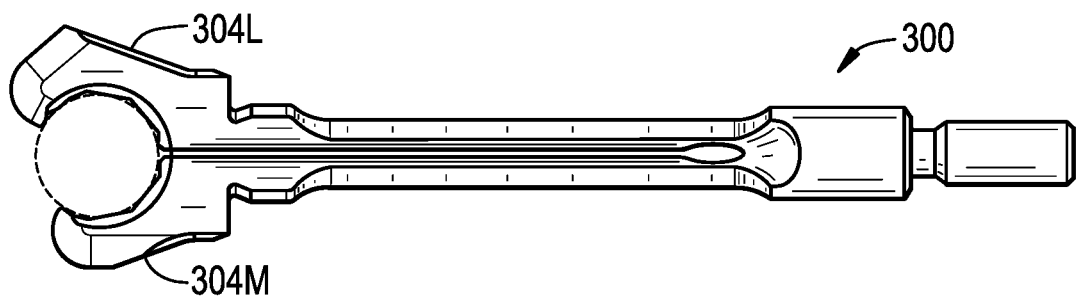
FIG. 3E is a top view of an inner member of the implant inserter of FIG. 3A.
Figure 3F:
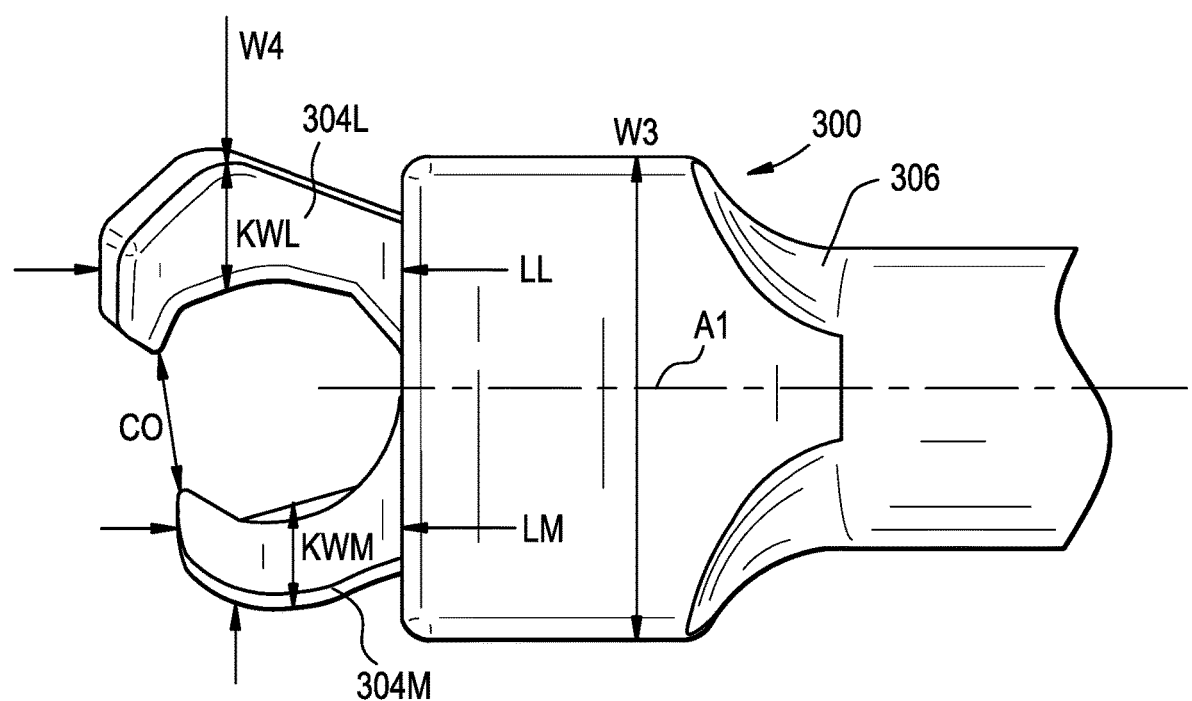
FIG. 3F is a detail top view of the implant inserter of FIG. 3A.

FIGS. 3A-3F illustrate an inserter instrument 300 in accordance with the present disclosure. The instrument 300 is shown in FIGS. 3A and 3B with an implant 302 loaded into the inserter (FIG. 3A) and unloaded (FIG. 3B). The instrument 300 is shown in FIGS. 3C and 3D in a closed position (FIG. 3C) and an open position (FIG. 3D). FIGS. 3E and 3F show detailed views of the instrument 300. As shown, the inserter instrument 300 can have a reduced geometry as compared to the inserter instrument 200 of FIG. 2.

The medial jaw 304M of the instrument 300 can have a length LM that is shorter than the length LL of the lateral jaw 304L. The lengths LM, LL can be measured as the degree to which the jaws 304M, 304L protrude from the outer member 306 when the instrument 300 is in the closed position. The ratio LM:LL can be about 5:7 in the closed position. The ratio LM:LL can be in the range of about 0.5:1 to about 0.9:1 in the closed position. The medial jaw 304M can be shorter than the medial jaw 204M of FIG. 2, and the lateral jaw 304L can be longer than the lateral jaw 204L of FIG. 2.

The outer knuckle of the medial jaw 304M can be removed or reduced, such that the medial jaw has a knuckle width KWM that is less than the knuckle width KWL of the lateral jaw 304L. The outer knuckle of the lateral jaw 304L can be removed or reduced instead or in addition. The knuckle widths KWM, KWL can be equal. The ratio KWM:KWL can be about 0.86:1. The ratio KWM:KWL can be in the range of about 0.8:1 to about 0.9:1.

The medial jaw 304M can be asymmetrical to the lateral jaw 304L. The claw opening distance CO when the instrument is in the closed position can be the same or substantially the same as in the instrument 200 of FIG. 2. By maintaining the claw opening distance, claw grip strength can be optimized, e.g., for implant repositioning. The claw opening can be oriented at an oblique angle with respect to the central longitudinal axis A1 of the outer member 306.

The distal end of the outer member 306 can have a width W3 that is less than the width W1 of the outer member 206 of FIG. 2. The width W3 can be less than the maximum outer width W4 of the jaws 304M, 304L when the instrument is in the closed position. The width W3 can be slightly larger than the maximum outer width W4 of the jaws 304M, 304L when the instrument is in the closed position. The jaws 304M, 304L can be off-center from the outer member 306 when the instrument is in the closed position. The distance between the maximum lateral extent of the lateral jaw 304L and the central longitudinal axis A1 of the outer member 306 can be greater than the distance between the maximum medial extent of the medial jaw 304M and the axis A1 when the instrument is in the closed position.

The maximum lateral extent of the lateral jaw 304L can be lateral to the maximum lateral extent of the outer member 306 when the instrument is in the closed position. In other words, the lateral jaw 304L can protrude laterally from the outer member 306 when the instrument is in the closed position. The maximum medial extent of the medial jaw 304M can be lateral to the maximum medial extent of the outer member 306 when the instrument is in the closed position. The maximum medial extent of the medial jaw 304M can be flush with or equal to the maximum medial extent of the outer member 306 when the instrument is in the closed position. In other words, the medial jaw 304M can be configured such that it does not protrude medially from the outer member 306 when the instrument is in the closed position and/or such that it is recessed from the outer member 306 in the medial direction. The maximum medial extent of the medial jaw 304M can be less than the maximum medial extent of the implant 302 when the implant is loaded into the instrument as shown in FIG. 3A. The maximum medial extent of the outer member 306 can be less than the maximum medial extent of the implant 302 when the implant is loaded into the instrument as shown in FIG. 3A. As also shown in FIG. 3A, the medial jaw 304M can overhang the implant 302 by a medial overhang distance OM. The distance OM can be less than the corresponding distance in the inserter 200 of FIG. 2. In some embodiments, the distance OM can be zero or negative, e.g., such that the medial jaw 304M does not protrude or overhang the implant in the medial direction.

The above-described geometry, including the reduced dimension of the medial jaw 304M and/or of the distal end of the outer member 306, can advantageously allow the instrument 300 to be shifted more in the medial direction, allowing a more medial approach to the disc space and reducing the invasiveness of the procedure. The geometry of the jaws 304 can also facilitate release of the implant 302 from the instrument 300 when desired, particularly in the case of more medial approaches. For example, as noted above, the claw opening CO can be oriented at an oblique angle with respect to a central longitudinal axis of the outer member 306.

Except as described herein and as will be readily appreciated by a person having ordinary skill in the art in view of the present disclosure, the structure and operation of the inserter instrument 300 can be the same as that of the instruments described in U.S. Publication No. 2011/0106259 entitled "SELF-PIVOTING SPINAL IMPLANT AND ASSOCIATED INSTRUMENTATION." The instrument 300 can include any of the features described in the above reference.

Figure 4A:
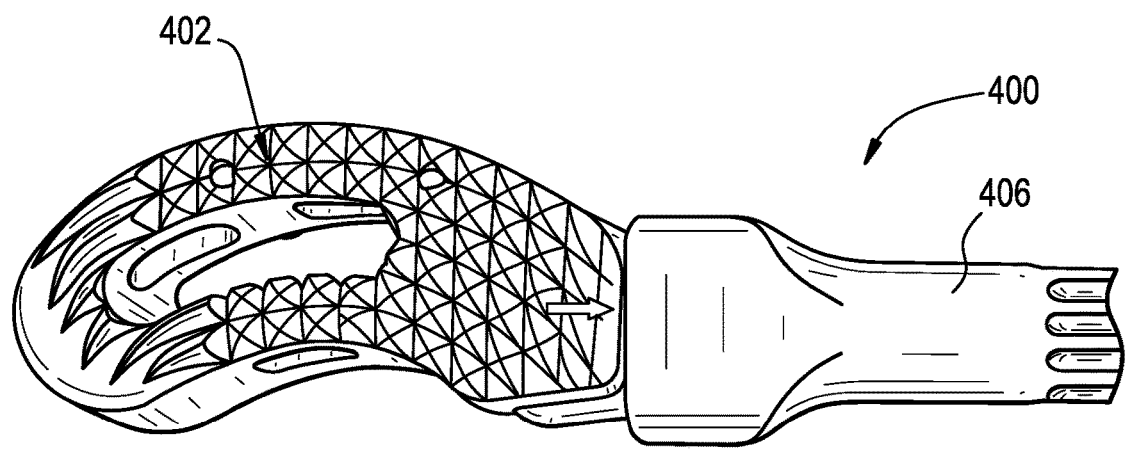
FIG. 4A is a top view of another implant inserter in accordance with the present disclosure, shown with an implant loaded into the inserter.
Figure 4B:
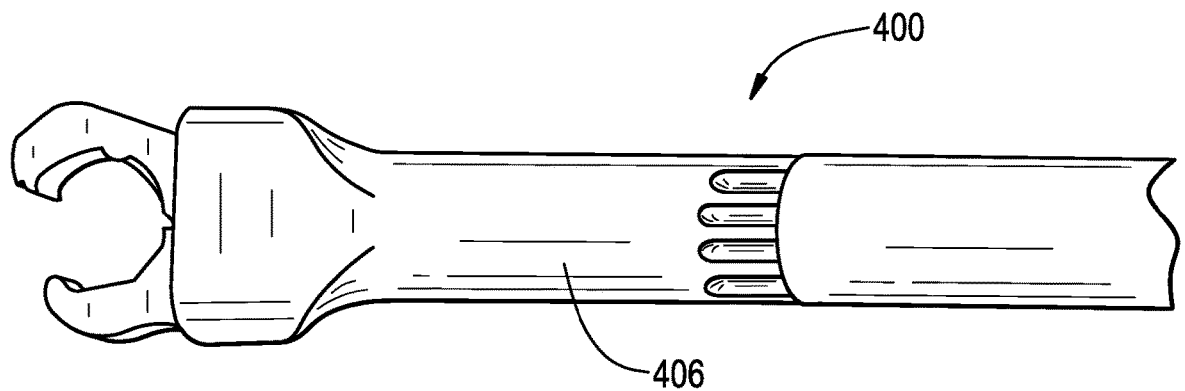
FIG. 4B is a top view of the implant inserter of FIG. 4A, shown in an unloaded configuration.

FIGS. 4A and 4B illustrate top views of another inserter instrument 400 in accordance with the present disclosure, shown with an implant 402 loaded into the inserter (FIG. 4A) and unloaded (FIG. 4B). As shown, the distal end of the outer member 406 can have a gradual, atraumatic taper with smoothly curved transitions between each outer face of the outer member, thereby reducing the risk of tissue damage as the inserter instrument 400 is passed through patient anatomy.

Figure 5A:
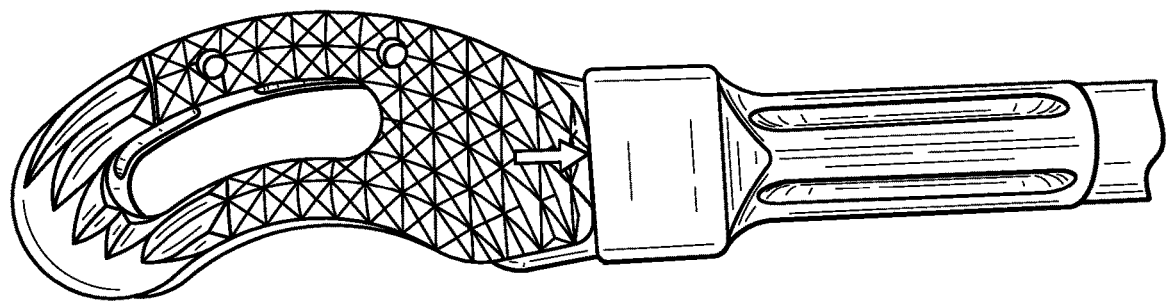
FIG. 5A is a top view of an implant inserter in accordance with the present disclosure, shown with an implant loaded into the inserter.
Figure 5B:
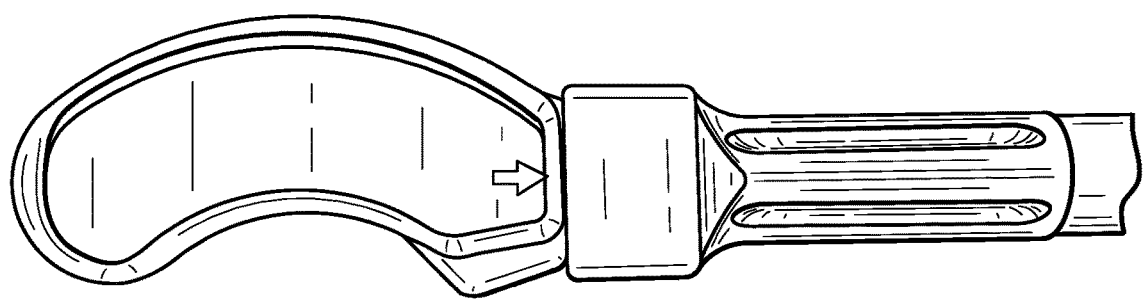
FIG. 5B is a top view of the implant inserter of FIG. 5A, shown with a trial spacer loaded into the inserter.

As shown in FIGS. 5A and 5B, the inserter instruments disclosed herein can be used to deliver various implants or objects to a surgical site, such as a fusion cage (FIG. 5A) or a trial spacer (FIG. 5B).

In use, the instrument can be cleaned and/or sterilized to prepare the instrument for surgery. A fusion cage or other implant can be loaded onto the instrument and clamped by the jaws, as shown in FIG. 3A. The instrument can then be used to deliver the implant to a target site within a patient, for example by passing the implant into a spinal disc space through a minimally-invasive working channel or an open approach. The instrument can be inserted using a PLIF approach, a TLIF approach, a medially-shifted PLIF approach, a medially-shifted TLIF approach, and so forth. Once the implant is disposed within the disc space, or at any other time desired by the user, the instrument can be disconnected from the implant and the surgical procedure can be completed using known techniques.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can be rigid or flexible. Device sizes can also vary greatly, depending on the intended use and surgical site anatomy. Furthermore, particular components can be formed from a different material than other components. One or more components or portions of the instruments can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The instruments and methods disclosed herein can be used in minimally-invasive surgery and/or open surgery. While the instruments and methods disclosed herein are generally described in the context of spinal surgery on a human patient, it will be appreciated that the methods and instruments disclosed herein can be used in any type of surgery on a human or animal subject, in non-surgical applications, on non-living objects, and so forth.

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

All papers and publications cited herein are hereby incorporated by reference in their entirety. Although specific embodiments are described above, it should be understood that numerous changes may be made within the spirit and scope of the concepts described. Accordingly, the disclosure is not to be limited by what has been particularly shown and described, except as indicated by the appended claims.

The invention claimed is:

1. A surgical instrument, comprising:
    an outer member having a central longitudinal axis; and
    an inner member having a medial jaw and a lateral jaw with the medial jaw configured to be located closer to a patient's spine than the lateral jaw, the inner member being axially translatable within an inner passage of the outer member to move the jaws towards one another to a closed position, thereby grasping an implant,
    wherein a distance between a maximum lateral extent of the lateral jaw and a central longitudinal axis of the outer member is greater than a distance between a maximum medial extent of the medial jaw and the central longitudinal axis of the outer member when the jaws are in the closed position.

2. The instrument of claim 1, wherein the medial jaw has a length that is less than a length of the lateral jaw when the jaws are in the closed position.

3. The instrument of claim 1, wherein the medial jaw has a knuckle width that is less than a knuckle width of the lateral jaw.

4. The instrument of claim 1, wherein the medial jaw is asymmetrical to the lateral jaw.

5. The instrument of claim 1, wherein a claw opening distance between the medial and lateral jaws is oriented at an oblique angle with respect to the central longitudinal axis of the outer member.

6. The instrument of claim 1, wherein a distal end of the outer member has a width that is less than a maximum outer width of the medial and lateral jaws when the jaws are in the closed position.

7. The instrument of claim 1, wherein a maximum medial extent of the medial jaw is less than or equal to a maximum medial extent of the outer member when the jaws are in the closed position.

8. The instrument of claim 1, wherein a maximum medial extent of the medial jaw is less than or equal to a maximum medial extent of an implant loaded into the instrument when the jaws are in the closed position.

9. The instrument of claim 1, wherein the instrument is configured to grasp an implant between the medial and lateral jaws of the inner member such that the medial jaw does not protrude or overhang the implant in a medial direction.

10. A surgical method, comprising:
    coupling an implant to an inserter, the inserter including an outer member and an inner member having a medial jaw and a lateral jaw that extend distally from a distal-most end of the outer member, the distal-most end of the outer member having a width that is less than a maximum outer width of the medial and lateral jaws when the jaws are in a closed position, such that the medial jaw of the inserter does not protrude or overhang the implant on at least a first side thereof;

passing the implant into a disc space between two vertebrae such that the first side faces in a medial direction toward a patient's spinal column; and releasing the implant from the inserter.

11. The method of claim 10, wherein coupling the implant to the inserter includes passing a portion of the implant into an opening between the medial jaw and the lateral jaw of the inserter and moving the jaws toward one another to clamp the implant.

12. The method of claim 11, wherein moving the jaws toward one another includes distally advancing the outer member relative to the inner member on which the jaws are formed.

13. The method of claim 12, wherein releasing the implant from the inserter includes proximally withdrawing the outer member relative to the inner member.

14. The method of claim 10, wherein passing the implant into the disc space is done using any of a PLIF approach, a TLIF approach, a medially-shifted PLIF approach, and a medially-shifted TLIF approach.

15. A surgical instrument, comprising:

an outer member having a central longitudinal axis; and an inner member having a medial jaw and a lateral jaw that extend distally from a distal-most end of the outer member, the inner member being axially translatable within an inner passage of the outer member to move the jaws towards one another to a closed position, thereby grasping an implant;

wherein the distal-most end of the outer member has a width that is less than a maximum outer width of the medial and lateral jaws when the jaws are in the closed position, wherein the medial jaw and the lateral jaw are asymmetrical to one another such that, when the jaws are in the closed position, only the lateral jaw extends beyond the maximum width of the distal-most end of the outer member.

\* \* \* \* \*